Figure 2:
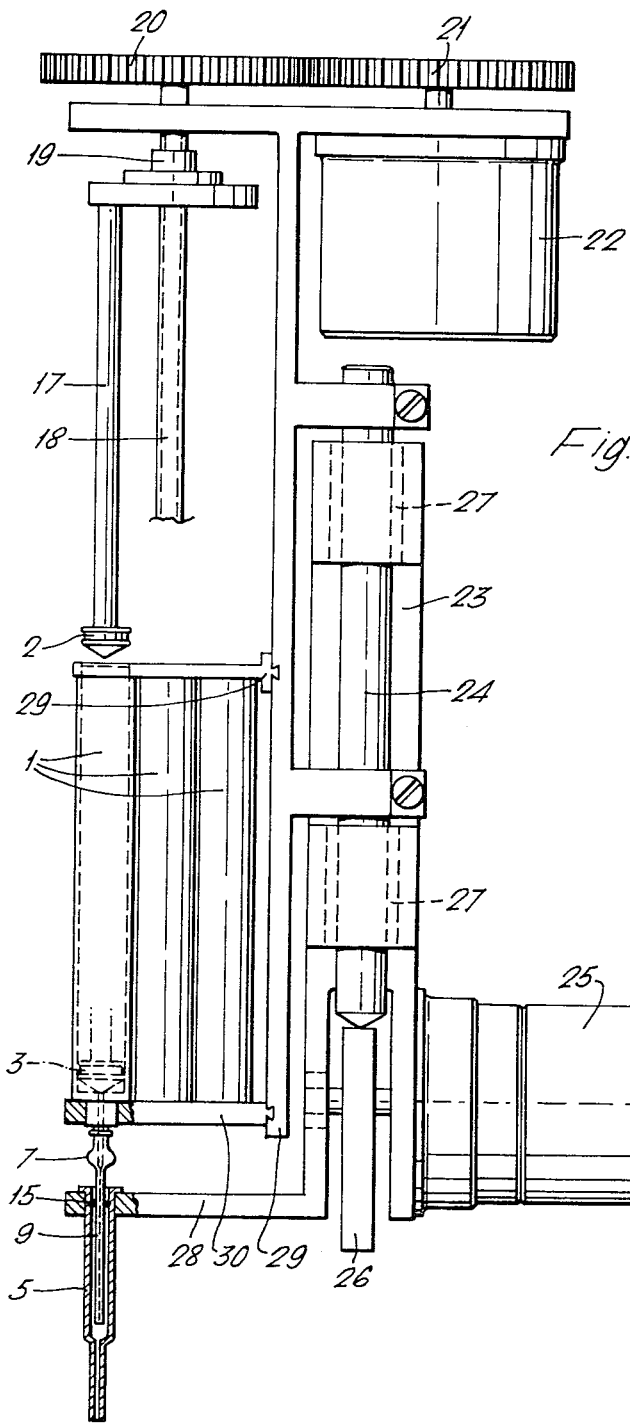

United States Patent [19]

Suovaniemi et al.

[11] 4,237,094
[45] Dec. 2, 1980

[54] APPARATUS FOR PRECISE MUTUAL DILUTION AND DOSAGE OF LIQUIDS

[75] Inventors: Osmo A. Suovaniemi; Pertti Ekholm, both of Helsinki; Esko Kaukanen, Espoo, all of Finland

[73] Assignee: Kommandiittiyhtio Finnpipette Osmo A. Suovaniemi, Helsinki, Finland

[21] Appl. No.: 1,396

[22] Filed: Jan. 5, 1979

[30] Foreign Application Priority Data

Jan. 10, 1978 [FI] Finland ................................ 780069

[51] Int. Cl.³ ............................................. G01N 1/14
[52] U.S. Cl. ............................. 422/100; 73/425.4 P; 73/425.6; 422/103; 222/158
[58] Field of Search ................. 422/61, 102, 103, 100; 73/425.4 P, 425.6, 425.4 R; 222/57, 41, 163, 398, 158

[56] References Cited

U.S. PATENT DOCUMENTS

| | | | |
|---|---|---|---|
| 3,106,845 | 10/1963 | Dimmick | 73/425.6 |
| 3,192,969 | 7/1965 | Baruch et al. | 422/100 X |
| 3,525,592 | 8/1970 | Buckley | 422/100 |
| 3,572,130 | 3/1971 | Goldsmith | 422/100 X |
| 3,800,984 | 4/1974 | Phelan | 422/100 |
| 3,834,590 | 9/1974 | Robinson et al. | 73/425.6 |
| 3,935,734 | 2/1976 | Keegan | 73/425.6 |
| 4,016,765 | 4/1977 | Lee | 73/425.6 |
| 4,061,037 | 12/1977 | Keegan | 73/425.6 |
| 4,130,394 | 12/1978 | Negersmith | 73/425.4 R |

FOREIGN PATENT DOCUMENTS

| | | |
|---|---|---|
| 283644 | 1/1928 | United Kingdom . |
| 333093 | 8/1930 | United Kingdom . |
| 1061125 | 3/1967 | United Kingdom . |
| 1202079 | 8/1970 | United Kingdom . |
| 1314234 | 4/1973 | United Kingdom . |
| 1334712 | 10/1973 | United Kingdom . |
| 1483002 | 8/1977 | United Kingdom . |
| 1529252 | 10/1978 | United Kingdom . |

Primary Examiner—R. E. Serwin
Attorney, Agent, or Firm—Hopgood, Calimafde, Kalil, Blaustein & Lieberman

[57] ABSTRACT

The subject of the present invention is an apparatus for precise mutual dilution and dosage of liquids, which apparatus comprises a dilution and dosage unit consisting of two cylinder spaces of different volumes and cross-sectional areas, as compared with each other, and connected to a common intake and exhaust tip, as well as of pistons arranged into said cylinder spaces. According to the invention, in each dilution and dosage unit, the lower part of the smaller cylinder space forms the intake and exhaust tip and the piston in the smaller cylinder space consists of a tubular component whose upper part is opened into the lower part of the larger cylinder space of the dilution and dosage unit concerned. In each dilution and dosage unit, a part of the intake pipe to the larger cylinder operates as the piston of the smaller cylinder

5 Claims, 4 Drawing Figures

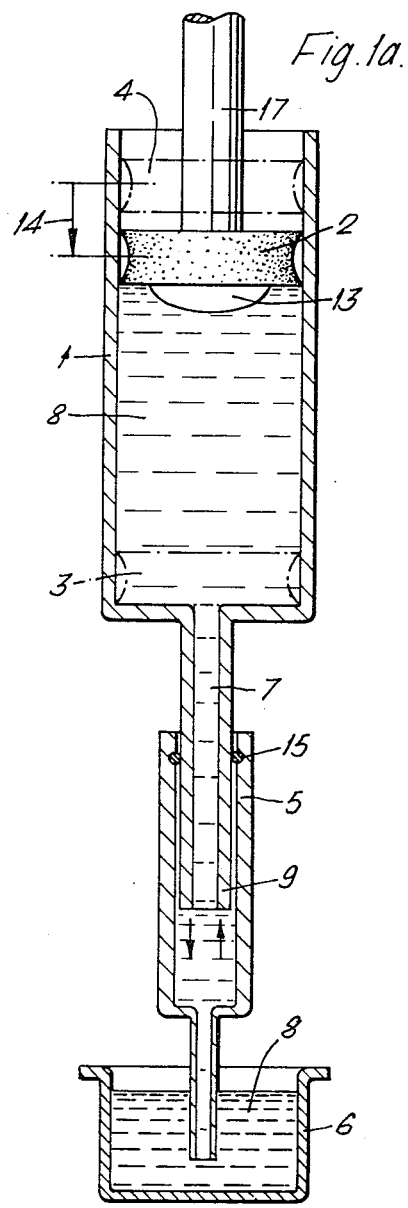
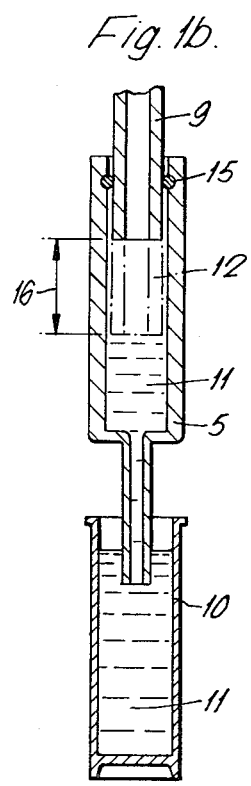

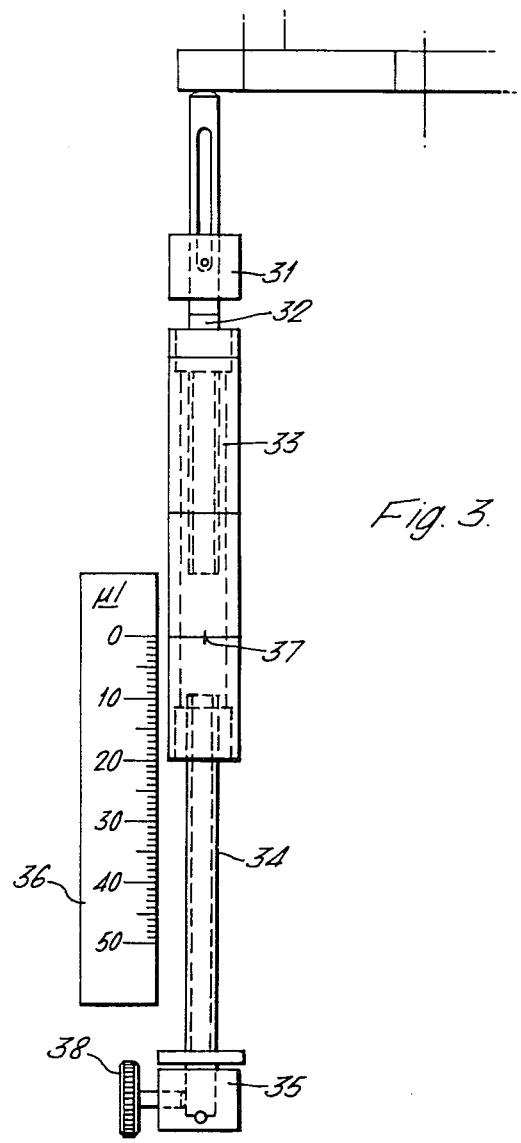

APPARATUS FOR PRECISE MUTUAL DILUTION AND DOSAGE OF LIQUIDS

The subject of the present invention is an apparatus for precise mutual dilution and dosage of liquids, such as samples and reagents, said apparatus comprising one or several parallel dilution and dosage units, which unit includes two cylinder spaces with different volumes and cross-sectional areas, as compared with each other, and connected to a common intake and exhaust tip, as well as pistons arranged into said cylinder spaces.

As a rule, for mutual dilution and dosage of liquids, such as samples and reagents, several pipettes of different volumes have been used, whose use is slow and unprecise in the case of large liquid quantities. Therefore, manually or electrically operated liquid dosage and dilution devices have also been developed, which comprise either one or several channels. As a rule, these devices include several cylinders and pistons as well as, between them, one or several valves, which make the devices complicated and expensive.

The diluting apparatus in accordance with the present invention has been developed in order to eliminate these drawbacks. The apparatus includes no valves at all, but the precise dosage and mixing of two different liquids, e.g. reagent and sample, is achieved by means of two separate piston movements in one and the same intake and exhaust channel.

The apparatus in accordance with the invention is mainly characterized in that, in each dilution and dosage unit, the lower part of the smaller cylinder space forms the intake and exhaust tip or is connected to the intake and exhaust tip and that the piston in the smaller cylinder space consists of a tubular component whose upper part is opened or connected to the lower part of the larger cylinder space of the dilution and dosage unit concerned, whereby, in each dilution and dosage unit, a part of the intake pipe into the larger cylinder operates as the piston of the smaller cylinder and whereby the passage of the liquid sucked into the larger cylinder is arranged so that, when exhausted, the liquid flushes the entire intake and exhaust channel and the smaller cylinder space.

The apparatus in accordance with the present invention comes out more closely from the following description and from the attached drawings, wherein FIGS. 1a and 1b are side views of the principle of operation of the dilution and dosage unit of the apparatus in accordance with the present invention, FIG. 2 is a schematical side view of an apparatus in accordance with the invention as a multi-channel embodiment, and FIG. 3 shows a limiting micrometer intended for controlling the stroke length of the piston and at the same time the volume of the samples in the apparatus in accordance with the invention.

FIG. 1a shows the main cylinder 1 of the diluting apparatus, whose piston 2 can be moved continuously or stepwise either manually or by means of a motor, e.g. by means of an electrical step motor and screw transmission. At the first step of dilution, the piston 2 is driven from its lower position 3 to the upper position 4, whereby liquid, e.g. reagent 8, flows from a vessel 6 placed underneath the tip 5, into the cylinder 1 and fills practically the entire cylinder. Only the quantity of air 13 included in the intake channel 7 and in the tips 5, which quantity has been made very small in relation to the entire volume of the cyliner 1, is sucked into the cylinder 1 at the beginning.

At the beginning of the second step of the dilution, the intake channel 7 as well as the piston 9 are full of liquid 8 after the first step. In the second step of the dilution, the liquid underneath the tip 5 is replaced by a new liquid (FIG. 1b), e.g. a tube or set of tubes 10 with the sample, from which the liquid, e.g. the sample 11, is sucked into the tip 5. The volume of the secondary movement is selected so that the quantity of the liquid, e.g. of the sample, is not larger than the exchangeable tips 5 of the diluting apparatus.

In the second step of dilution, the piston 9 is moved upwards, which piston consists of a part of the intake channel 7, which is by means of a sealing means 15 sealed to the tip 5. The cylinder 1 together with the piston 2 move along with the piston 9 so that they have no movement in relation to each other, and thereby the liquid quantity 8 in cylinder 1 remains constant. The piston 9 may also be connected to the lower part of the cylinder space 1 by means of a hose or tube, whereby it is, of course, sufficient that the piston 9 alone is moved.

In the third step of the dilution, the sample 11 is removed from the tip 5 into a desired vessel, e.g. set of assay cuvettes (not shown in the drawing), by driving the secondary piston 9 back to its lower position 12.

In the fourth step, the piston 2 of the main cylinder 1 is driven the distance of a desired, adjustable step 14 down, whereby the liquid 8, e.g. the reagent, flows through the entire intake channel, piston 9 and the tip 5 into the vessel, e.g. a set of cuvettes, and at the same time flushes the tip 5 clean of the sample liquid. The dilution is produced in the vessel when the liquids 8 and 11 are mixed with each other. The dilution ratio can be fixed precisely by means of the ratio of the area of the piston 2 and of the step 14 to the area of the piston 9 and to the stroke length 16. New dilutions may be performed after the first one by always driving the piston 2 of the main cylinder 1 downwards the distance of the precise step 14 at a time.

It is typical of the invention that the intake pipe 7 operates as one piston 9 of the apparatus and that the sample tip 5 is always flushed clean by means of the reagent liquid 8, which is dosed stepwise. It is easy to apply the invention in a multi-channel form into a very small space, whereby an efficient diluting device is provided for large sample quantities.

FIG. 2 shows an embodiment of the invention in a multi-channel form which is operated electrically.

The main cylinders 1 attached to the stand 30 constitute a group in which the pistons 2 are moved by means of an electrical motor 22 and a transmission mechanism consisting of cogwheels 20 and 21, of a screw 18, and of a nut 19 fitted onto the screw 18. When the electrical motor 22 rotates the cogwheel 21, the latter transfers the movement to the cogwheel 20, which further rotates the screw 18. When the screw 18 rotates, it drives the nut 19 either up or down depending on the direction of rotation of the electrical motor 22, which can be reversed. The pistons 2 are by means of arms 17 connected to the nut 19 and consequently move along with the nut 19. Of course, the revolutions of the electrical motor or of the screw are counted in a way in itself known, so that the distance run by the piston 2 and, correspondingly, the liquid volume sucked into, or exhausted from, the cylinder 1 are known precisely. When the pistons 2 are in the upper position, as is shown in FIG. 2, the cylinders 1 can be removed and replaced easily in the stand 30 when required, by means of an instant lock 29, e.g. for the purpose of washing or for a different reagent type.

The movement of the pistons 9 is produced by means of an electrical motor 25 and by means of an eccentricity 26 on its axle. When the electrical motor 25 rotates the eccentricity 26, it further moves a rod 24 gliding on guides 27 mounted on the frame 28. The stand 30 with the main cylinder 1, the electrical motor 22, and the transmission mechanism is connected to the rod 24. Intake channels 7 departing from the lower end of the cylinders 1 in the stand 30 constitute the group of pistons 9 in the tips 5 attached to the frame 28 of the apparatus, to which tips the pistons 9 are sealed by means of sealing means 15. Thus, when the motor 25 rotates, the stand 30 with all the equipment connected to same, including the pistons 9 moving inside the tips 5, moves. The eccentricity 26 is preferably turning back and forth between two predetermined limit positions, whereby it produces a raising and lowering movement of constant magnitude on the rod 24. This raising and lowering movement can be easily adjusted and limited to a shorter length by between the frame 28 and the stand 30 providing a preferably continuously adjustable limiting means, such as a limiting micrometer (FIG. 3).

The dilutions are performed with the apparatus in the way described above by alternately operating the electrical motors 22 and 25.

FIG. 3 illustrates the limiting micrometer intended for controlling the stroke length of the pistons 9 and, at the same time, for adjusting the volume of the samples.

The base component 35 is fastened to the frame 28 of the apparatus. By means of screws 38 belonging to the base component, it is possible to lock a screw 34 in position. The rise of this screw is in this particular example case 1 mm. On this screw, a bushing 33 rotates whose lower end is provided with threading so as to fit onto the screw 34. The upper end of the bushing 33 is in this particular example cases provided with threading of 1.4 mm. The screw 32 passes in this thread, and the rotation of this screw is prevented by the bushing 31. The threading of 1.4 mm is arranged so that, when the bushing 33 is turned, the screw 32 moves towards the frame 28 and the base component 35 with a rise equal to the difference between the rises of the screws 32 and 34, which is in this particular example case 0.4 mm. It is possible to provide the bushing 33 with a marking line 37, at which it is possible to read a scale 36. The scale 36 is extended in accordance with the real movement. The line 37 passing around the bushing 33 may be provided with a part scale corresponding one revolution. In order to match the movement of the component 32 to the scale, the groove and bushing arrangement may be made in such a way adjustable that the screw 32, when it moves, may turn a little with an effect on the rise of the thread on the screw 32. Calibration is achieved by this means.

The invention may, of course, also have other embodiments, which do, however, not differ from each other functionally.

What we claim is:

1. Apparatus for the precise dilution of liquid comprising:
    a first cylinder;
    an intake and exhaust tube, coupled for liquid communication to said first cylinder;
    piston means coupled to said first cylinder to cause intake and exhaust of liquid into and out of said first cylinder through said intake and exhaust tube;
    a second cylinder having a smaller cross-sectional area than said first said cylinder;
    at least a portion of said intake and exhaust tube being slidably disposed within said second cylinder, to define a piston within said second cylinder;
    liquid intake and exhaust means coupled to said second cylinder to thereby permit the intake and exhaust of said liquid into said first and second cylinders; and
    said piston means in said first cylinder and said intake and exhaust tube disposed in said second cylinder being operable independently of each other, said intake and exhaust tube of said first cylinder forming the piston of said second cylinder to intake and exhaust liquid into and out of said second cylinder when said intake and exhaust tube is moved relative to said second cylinder.

2. The apparatus as claimed in claim 1 wherein said piston means are slidably disposed in said first cylinder.

3. The apparatus as claimed in claim 1 wherein said intake and exhaust tube of said first cylinder is rigid and extends from a lower portion of said first cylinder.

4. The apparatus as claimed in claim 1 wherein said first and second cylinders are remote from each other, said intake and exhaust tube of said first cylinder is flexible and couples said first and second cylinders together.

5. The apparatus as claimed in claim 1 wherein said apparatus further includes motor driven means for operating said piston means and for displacing said first and second cylinders with respect to each other.

* * * * *